United States Patent [19]

Porteous

[11] Patent Number: 4,844,308
[45] Date of Patent: * Jul. 4, 1989

[54] DENTAL DISPENSING CUP WITH INTEGRATED FINGER MOUNT

[76] Inventor: Don D. Porteous, 2794 Moraga Dr., Los Angeles, Calif. 90024

[*] Notice: The portion of the term of this patent subsequent to Jan. 5, 2005 has been disclaimed.

[21] Appl. No.: 140,303

[22] Filed: Dec. 31, 1987

Related U.S. Application Data

[63] Continuation-in-part of Ser. No. 4,543, Jan. 16, 1987, Pat. No. 4,717,057.

[51] Int. Cl.⁴ .............................................. B65D 1/00
[52] U.S. Cl. ................... 224/217; 206/63.5
[58] Field of Search .............. 224/217, 219, 236, 241, 224/251, 267; 433/163; 206/63.5, 815

[56] References Cited

U.S. PATENT DOCUMENTS

| 1,955,175 | 4/1934 | Crowther | 206/63.5 |
| 2,222,741 | 11/1940 | Bush | 224/217 |
| 2,539,940 | 1/1951 | Abramson | 224/217 |
| 2,665,479 | 1/1954 | Weldon | 433/163 |
| 2,970,379 | 2/1961 | Hardgrove | 433/163 |
| 3,327,391 | 6/1967 | Malm | 206/63.5 |

Primary Examiner—Renee S. Luebke
Attorney, Agent, or Firm—Donald Diamond

[57] ABSTRACT

A dental paste cup is provided which comprises a cup having an open mouth defined by a rim, a removable closure overlying the open mouth and engaging the rim, and a finger mount extending adjacently and circumferentially from the rim, in a ring-like manner, and terminating in an open end proximate to the rim to thereby provide a slide-resistant grip on a support finger. In one embodiment, the end segment, which is releasably attached to the outer rim of the cup, passes through an aperture in the finger mount into alignment with an outer extension of the closure, which is releasably secured to the inner rim of the cup. The application of a vertical squeezing force to the finger mount disengages the end segment from the rim and permits the end segment to bear against the outer extension of the closure and thereby effect displacement of the closure from the mouth of the cup. In an alternative embodiment, the finger mount has a continuous construction and the closure is mechanically secured to the rim of the cup or the closure comprises heat sealable material that is heat sealed to the rim of the cup.

9 Claims, 2 Drawing Sheets

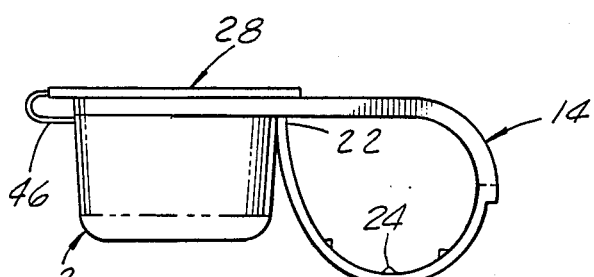
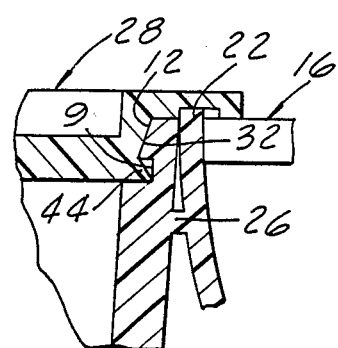
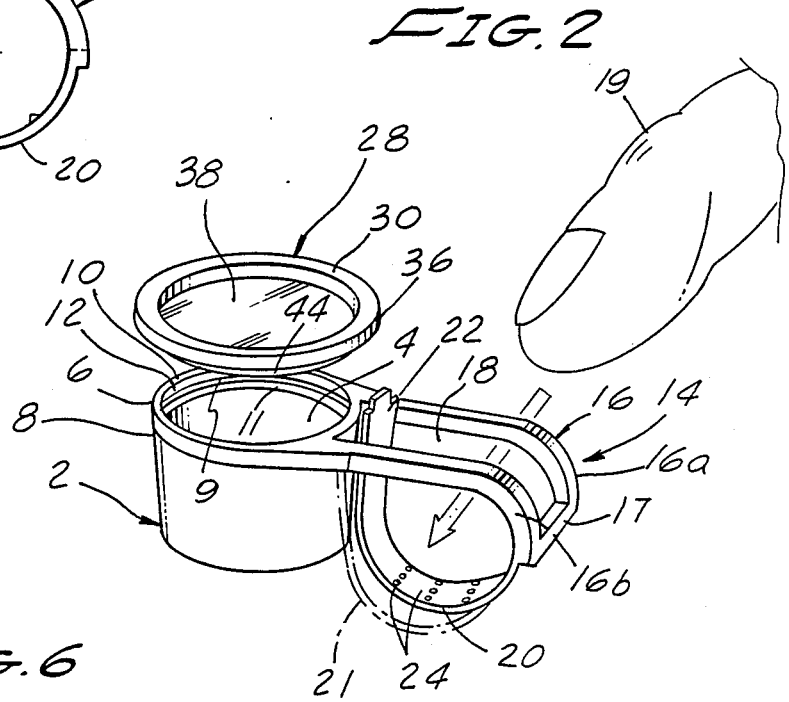
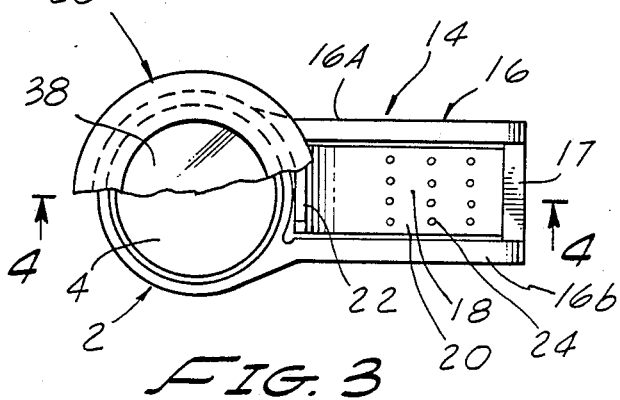
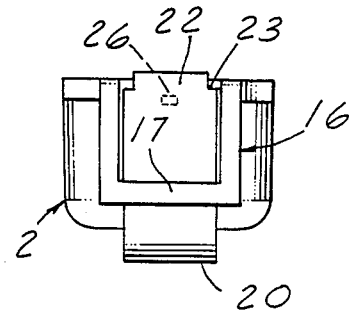
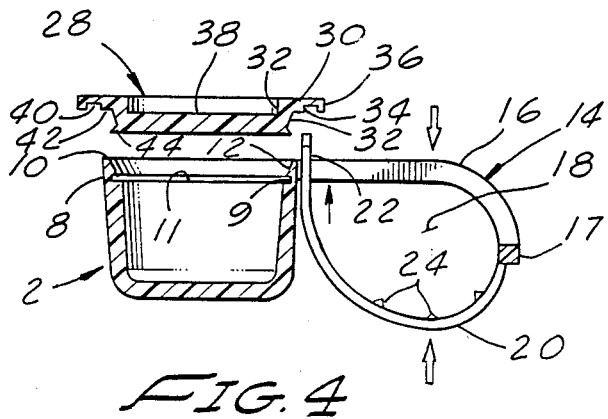
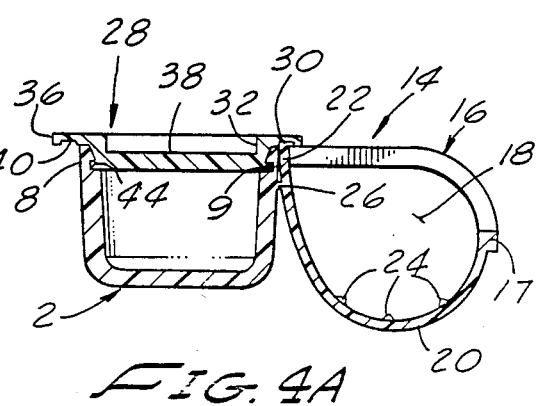

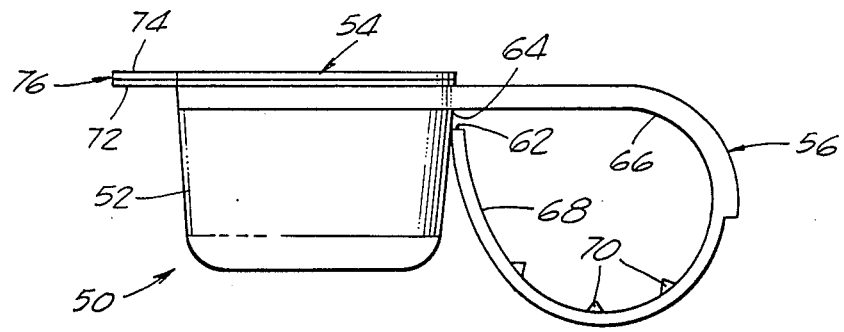
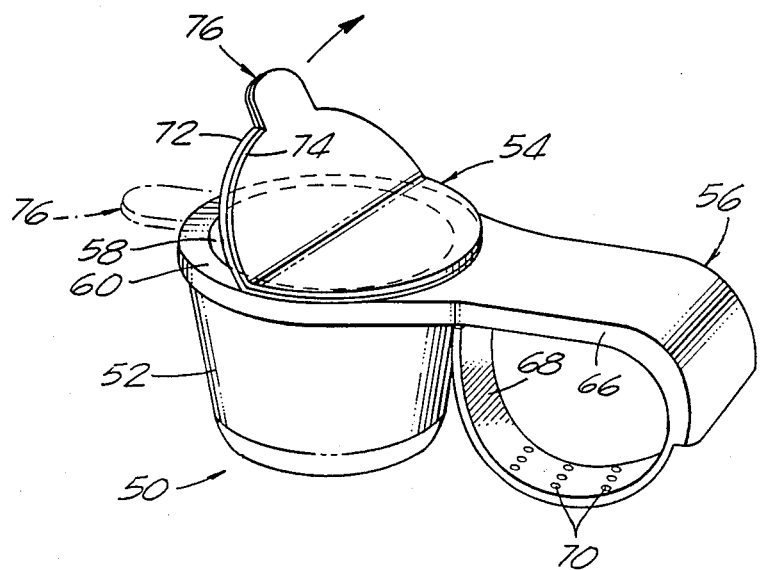

DENTAL DISPENSING CUP WITH INTEGRATED FINGER MOUNT

CROSS-REFERENCE TO RELATED APPLICATION

This application is a continuation-in-part of U.S. patent application Ser. No. 4,543, filed Jan. 16, 1987 and entitled Dental Paste Cup With Integrated Finger Mount, now U.S. Pat. No. 4,717,057.

BACKGROUND OF THE INVENTION

1. Field of the Invention

This invention relates to dental dispensing cups and, more particularly, to dental dispensing cups which incorporate a finger mount having improved finger gripping characteristics.

2. Prior Art

In one packaging format, dental polishing paste adapted for use in dental practice has been supplied to the dental profession in disposable cups, sized for individual patient usage. In this format, the dental paste cup generally comprises a cylindrical container having an open mouth which is continuous with an outwardly disposed lateral flange. A closure in the form of a thin cover sheet overlies the mouth of the container and is secured to the upper surface of the lateral flange. The closure includes a laterally extending, pull-open tab to facilitate complete removal of the closure at the time of use and thereby permit unimpeded access to the dental paste in the container.

The aforesaid dental paste cup is adapted to be used with a sterilizable and reusable, metallic, finger-mountable, cup holder. In an illustrative prior art embodiment holder, which is constructed from thin sheet metal, generally comprises a cylindrical member that is continuous with an upwardly, outwardly and downwardly extending, finger-mountable member having its terminus in substantial spaced relationship to the cylindrical member. The finger-mountable member, in this embodiment, has an inverted U-shaped or horseshoe-like configuration. In use, the body of the dental paste cup is passed through the cylindrical member so as to engage the top of this member with the underside of the cup's lateral flange. The U-shaped finger mount is then passed over the finger which provides a support for the holder-cup combination. Thereafter, the clinician removes the closure from the dental paste cup and dips the tip of a power actuated applicator into the cup to thereby obtain a suitable quantity of dental paste for use in polishing a patient's teeth. A significant problem associated with the repeated use of dental cup holders incorporating U-shaped finger grips is that such holders tend to slip and slide about the finger upon application of a dipping force to the contents of the dental cup.

2a. Prior Art, U.S. Patents

U.S. Pat. No. 3,327,391 (Malm, 1967) discloses a disposable, clear acetate, dental material cup containing dental medicaments or pumices and provided with a cellophane cover that may be heat sealed to the outwardly projecting rim of the cup, wherein the cup is adapted to be slip-fitted or snap-connected to a supporting, split, finger ring made of more permanent material since the ring is not considered to be disposable with the cup.

U.S. Pat. No. 2,970,379 (Hardgrove, 1961) discloses a sterilizable, vertically disposed and pivotally connected, two-compartment, finger supportable dental tray for holding plastic filling materials, dental cleaning compounds and medications wherein the upper compartment forms a closure for the lower compartment and the lower compartment is provided with a lateral ring or rim having a laterally extending flat plate that merges with a ring member characterized as a semi-circular continuation of the plate, extending downwardly therefrom, and has an open end portion deviating from a true semi-circle by protruding as a straight construction of the semi-circle.

SUMMARY OF THE INVENTION

An important object of this invention is to provide an integrated dental paste cup and finger mount which has improved finger-gripping characteristics to thereby resist slipping and sliding about the finger when force is applied to the cup in connection with the removal of dental paste.

Another object of this invention is to provide an integrated dental dispensing cup and finger mount together with a cover for the cup which are formed by the conversion of a suitable molding resin into finished packaged components that are adapted to be assembled into a finished product containing dental paste or other dental material, for individual usage, wherein the package is discarded after use to thereby save the time, cost and inconvenience involved in the sterilization of the metallic cup holders of the prior art.

These and other objects, features and advantages are accomplished by providing a dental dispensing cup comprising a cup having an open mouth defined by a rim, a removable closure overlying the open mouth and engaging the rim, and a finger mount extending circumferentially in an outward and downward direction from the rim of the cup and terminating in an open end proximate to the rim to thereby provide a slide-resistant grip on a support finger.

The rim of the cup includes an inner surface, a top surface and an outer surface with the inner surface advantageously being recessed and provided with a circumferential groove at its lower end. The removable closure has a substantially rigid construction and includes a laterally disposed peripheral flange that overlies the top of the rim and extends outwardly therefrom to thereby define an outer extension. The removable closure further includes a depending portion that is seated about and in slidable engagement with the inner surface of the rim. The lower end of the depending portion is advantageously provided with an outwardly disposed lateral tongue that is releasably engaged by the rim groove for releasably securing the closure to the cup.

The finger mount includes an aperture therethrough that extends outwardly from the cup rim. The open end of the finger mount passes through the aperture and into alignment with the underside of the closure outer extension whereby the application of a vertical squeezing force to the finger mount disengages the closure from the cup. To facilitate alignment of the open end of the finger mount with the outer extension of the closure, the finger mount can be releasably secured to the cup through a manually frangible connector disposed at or near the outer surface of the rim.

In contrast to the separate dental paste cup and metallic holder of the prior art, the present invention provides a disposable dental paste cup with an integrated finger mount having enhanced finger gripping characteristics to thereby resist slipping and sliding during use and, additionally, the integrated finger mount can be utilized to remove the closure from the cup.

The dental dispensing cup of this invention is readily manufactured from conventional materials by generally known methods of manufacture. A particularly suitable method of manufacture is injection molding of polyethylene resin, or similar plastic material, to thereby obtain components which, in assembled form, define a dental paste enclosure having an integrated finger mount for enhanced clinical usage.

In an alternative embodiment, the finger mount has a continuous construction and the closure is mechanically secured to the rim of the cup or the closure comprises heat sealable material that is heat sealed to the rim of the cup.

DESCRIPTION OF THE DRAWINGS

FIG. 1 is a side elevational view of an embodiment of the present invention showing a dental paste cup and closure therefor, with the closure having an outer extension and the cup incorporating an integrated finger mount having an open end segment disposed proximate to the rim of the cup;

FIG. 2 is a diagrammatic view of the dental paste cup depicted in FIG. 1 and shows the finger mount provided with an aperture through which the open end segment passes to engage and effect removal of the closure from the cup;

FIG. 3 is a top plan view of the dental paste cup depicted in FIG. 1 and shows the closure in fragmentary section to further show the open end of the finger mount disposed within a channel on the underside of the closure outer extension;

FIG. 4 is a transverse section along line 4—4 of FIG. 3;

FIG. 4a is a transverse section similar to FIG. 4 showing the closure engaging the cup rim and the finger mount attached to the cup by a frangible connector;

FIG. 5 is a rear elevational view of the dental paste cup depicted in FIG. 1, with the cover removed;

FIG. 6 is an enlarged, fragmentary, sectional view showing the tongue and groove assembly for releasably holding the closure to the cup;

FIG. 7 is a side elevational view of an alternative embodiment of the present invention showing a dental paste cup and closure therefor, with the closure being heat sealed to the rim of the cup and the cup incorporating an integrated finger mount having an open end segment disposed proximate to the rim of the cup.

FIG. 7A is a partially diagrammatic, perspective view of the dental paste cup depicted in FIG. 7 and shows the heat sealed closure partially removed from the rim of the cup and shows the finger mount having a continuous construction.

DETAILED DESCRIPTION

Referring now to the drawings and, in particular, FIGS. 1 and 2, there is shown a dental paste cup comprising a cup body 2 and a closure therefor 28, with the cup body being provided with an integrated finger mount 14.

The cup body 2 has an open mouth 4 defined by a rim 6 having an outer surface 8, a top surface 10 and an inner surface 12, with the inner surface of the rim being recessed and forming a shoulder 11 with the inner wall of the cup body. The lower end of the rim inner surface is provided with a circumferential groove 9.

The finger mount 14 extends outwardly from the rim of the cup, in a ring-like manner, and terminates in an open end segment 22 proximate to the cup outer rim 8, with the end segment including peripheral shoulder portion 23. The finger mount includes a first portion 16 and a second portion 20, with the first portion being formed by a pair of members 16a and 16b that are separated by an aperture 18 and joined at their distal ends by a cross-bar 17. The end sections of the members forming the first portion, as shown in FIGS. 1, 2 and 4, curve downwardly to the cross-bar 17 and the second portion 20 of the finger mount extends downwardly from the cross-bar and is curved inwardly and upwardly to terminate in the end segment 22 which passes through the aperture 18 into a position proximate to the cup outer rim. As shown in FIG. 2, the curvatures of the first portion 16 and the second portion 20 of the finger mount define an opening through which a finger 19 may be inserted and which serve to releasably grip the finger to thereby retain the cup 2 in a desired position on the finger. A plurality of ridges or risers 24 may advantageously be provided on the inner surface of the finger mount second portion 20 to enhance the gripping characteristics of the finger mount. A readily frangible connector 26 may advantageously be used to releasably secure the outer surface of the finger mount second portion 20 to the outer surface of the cup 2 at a locus proximate to the bottom of the rim outer surface 8. The frangible connector maintains the end segment 22 of the finger mount second portion in a suitable position and alignment to aid in the removal of closure 28 from the body of the cup.

The closure 28 releasably encloses the mouth 4 of the cup 2 and is formed with a peripheral flange 30 having a depending portion 32 and inner and outer skirts 34, 36. The depending portion 32 connects the peripheral flange 30 to the recessed closure surface 38 while the inner and outer skirts 34, 36 define an inverted channel 40. Inner skirt 34 forms a shoulder 42 with depending portion 32. The lower end of the depending portion 32 is provided with an outwardly disposed, circumferential tongue 44 that is adapted to be releasably engaged by the circumferential rim groove 9 to releasably secure the closure to the cup.

In the assembled package, the depending portion 32 of the closure 28 is seated about and in slidable engagement with the cup rim inner surface 12, the top of the cup rim 10 engages the closure shoulder portion 42, the closure tongue 44 is releasably engaged in the rim groove 9, the end segment 22 of the finger mount is releasably connected to the outer surface of the cup rim by a frangible connector 26, and the terminus of the end segment 22 is disposed within the closure inverted channel 40.

In use, the enclosed dental paste cup is provided to the clinician containing a dental paste or other suitable material for application to a patient. By applying a vertical squeezing force to the finger mount 14, as shown in FIG. 4, the clinician breaks the frangible connector 26 and causes the finger mount end segment 22 to disengage from a fixed position 21 and to bear against the outer extension of flange 30 which forces the closure tongue 44 out of the rim groove 9 and effects displacement of the closure from the mouth of the cup to thereby permit access to the contents within the cup. The clinician then inserts a finger 19 into the finger mount 14, where the curvature of the semi-rigid first portion 16, the curvature of the yieldable second portion 20, and the risers 24 on the inner surface of the second portion serve to prevent slipping and sliding of the finger mount on the support finger and to releasably retain the cup 2 in the desired position. The clinician then dips the tip of a power actuated applicator into the dental paste cup to obtain a suitable quantity of dental paste which is applied to a dental area in the usual manner. Upon completion of this aspect of the treatment, the dental paste cup, which is sized for individual patient usage, is discarded.

In a further embodiment of this invention, the closure 28 is pivotally hinged to the outer surface of the cup body 2 by a frangible strap hinge 46, as shown in FIG. 1. The attachment of the closure to the cup body through the strap hinge facilitates final assembly of the packaged product. Since the strap hinge has a frangible construction, it can be readily severed by the clinician following displacement of the closure from the cup or the strap hinge can be severed by the packager after the cup is filled with dental paste and the closure is secured to the rim of the cup.

The principal components of the dental paste cup, namely, the closure 28 and the cup 2 with an intergrated finger mount 14 may be readily manufactured by utilizing customary molding techniques with a suitable plastic resin such as polyethylene, polypropylene and the like.

Referring now to FIGS. 7 and 7A, there is shown, in an alternative embodiment, a plastic, disposable, dental dispensing cup 50 comprising a cup body 52 and a closure therefor 54, with the cup body being provided with an integrated finger mount 56.

The cup body 52 has an open mouth 58 defined by a lateral rim 60 that is contiguous with the upper end of the cup body. The finger mount 56 extends outwardly from the rim 60 of the cup, in a circumferential manner, and terminates in an open end 62 proximate to the underside juncture 64 of the finger mount with the rim 60. The finger mount 56, which has a continuous construction, includes a first portion 66 and a second portion 68. The first portion of the finger mount, which can be yieldable or semi-yieldable, has a substantially flat section that merges into a downwardly directed arcuate section, wherein the flat section extends outwardly from the rim of the cup and forms the top of the finger mount. The second portion 68 of the finger mount, which is yieldable and can have a reduced thickness with respect to the first portion of the finger mount, extends from the distal terminus of the first portion 66 in a downwardly and upwardly arcuate configuration and terminates in the open end 62. As shown in FIGS. 7 and 7A, the curvatures of the first portion 66 and the second portion 68 define an opening through which a finger is inserted and which serve to releasably grip the finger to thereby retain the cup in a desired position on the finger. A plurality of ridges or risers 70 may advantageously be provided on the inner surface of the second portion 68 to enhance the gripping characteristics of the finger mount.

A substantially flat, removable, closure 54 overlies the open mouth 58 of the cup body 52 and sealingly engages the rim 60 of the cup. The closure advantageously comprises heat sealable material which is heat sealed to the rim of the cup. In an illustrative embodiment, the closure comprises a laminated cover sheet having an inner face 72 of heat sealable material, such as polyethylene, and an outer face 74 comprising cellophane, paper, plastic, metalized plastic, aluminum foil or the like. The laminated cover sheet also includes a pull-tab 76 to facilitate removal of the cover at the time of use. In an alternative embodiment, the substantially flat closure 54 cooperatively engages the rim 60 of the cup to define a mechanical seal.

In use, the sealed dental dispensing cup is provided to the clinician containing a dental paste or other suitable material for application to a patient. After removing the heat sealed closure 54 by applying an appropriate upward force to the pull-tab 76, the clinician then inserts a finger into the finger mount 56, where the curvatures of the first and second portions 66, 68 and the risers 70 on the inner surface of the second portion serve to prevent slipping and sliding of the finger mount on the support finger and to releasably retain the cup in the desired position. The clinician then dips the tip of a power actuated applicator into the dental dispensing cup to obtain a suitable quantity of dental material which is applied to a dental area in the usual manner. Upon completion of this aspect of the treatment, the dental dispensing cup, which is sized for individual patient usage, is discarded.

The heat sealable laminated closure can be readily sealed to the rim of the cup by utilizing customary heat sealing equipment and procedures, while the body of the cup and its integrated finger mount can be fabricated from suitable plastic resins such as polyethylene, polypropylene and the like by utilizing customary molding techniques.

While in the foregoing description and accompanying drawings, there has been shown and described the preferred embodiment of this invention, it will be understood, of course, that minor changes may be made in the details of construction as well as in the combination and arrangement of parts without departing from the spirit and scope of the invention as claimed.

That which is claimed is:

1. A disposable dental dispensing cup, comprising:
   a molded plastic cup having an open mouth defined by a rim and containing dental material;
   a substantially flat, removable, closure overlying said open mouth and sealingly engaging said rim;
   a finger mount integrally molded with and extending circumferentially in an outward and downward direction from the rim of said cup and terminating in an open end proximate to said rim, and being elastically yieldable to provide a slide-resistant grip on a support finger.

2. The dental dispensing cup of claim 1 wherein said finger mount is defined by first and second portions, with said first portion projecting from the rim of the cup in said outward and downward direction, and wherein said first portion is semi-yieldable and said second portion is yieldable.

3. The dental dispensing cup of claim 2 wherein a plurality of finger-engaging risers extend from the inner, finger engaging surface of the second portion of said finger mount.

4. The dental dispensing cup of claim 1 wherein said closure comprises heat sealable material that is sealed to the rim of said dental dispensing cup.

5. The dental dispensing cup of claim 4 wherein said closure includes an inner face of heat sealable material and an outer face, with said inner face being heat-sealed to the rim of said dental dispensing cup.

6. The dental dispensing cup of claim 5 wherein the outer face comprises cellophane, paper, plastic, metalized plastic or aluminum foil.

7. The dental dispensing cup of claim 6 wherein the inner face is polyethylene and the outer face is aluminum foil.

8. The dental dispensing cup of claim 2 wherein the second portion of said finger mount has reduced thickness with respect to the first portion of said finger mount.

9. The dental dispensing cup of claim 1 wherein said closure is mechanically secured to the rim of said cup.

* * * * *